United States Patent [19]

Burkhart et al.

[11] Patent Number: 4,588,825

[45] Date of Patent: May 13, 1986

[54] INTERMEDIATES FOR THE SYNTHESIS OF 4-AMINO-4,5-DIHYDRO-2-FURANCARBOXYLIC ACID

[75] Inventors: Joseph P. Burkhart, West Chester; Gene W. Holbert, Loveland, both of Ohio

[73] Assignee: Merrell Dow Pharmaceuticals Inc., Cincinnati, Ohio

[21] Appl. No.: 712,318

[22] Filed: Mar. 13, 1985

Related U.S. Application Data

[63] Continuation of Ser. No. 540,745, Oct. 11, 1983, abandoned.

[51] Int. Cl.$^4$ .............. C07D 307/24; C07D 307/30; C07F 7/18
[52] U.S. Cl. .................................... 549/475; 549/480; 556/420; 560/160; 560/157; 560/171
[58] Field of Search ................ 549/475, 480; 556/420

[56] References Cited

U.S. PATENT DOCUMENTS 3,960,927  6/1976  Metcalf et al. .................. 560/38
4,524,076  6/1985  Metcalf et al. .................. 514/472

OTHER PUBLICATIONS

Oppolzer et al, JACS, vol. 104 (1982) pp. 4978 & 4979.
Allan et al, Chemical Abstracts, vol. 101 (1984) 54821r.

*Primary Examiner*—Richard L. Raymond
*Attorney, Agent, or Firm*—Raymond A. McDonald

[57] ABSTRACT

This application relates to a stereospecific process for preparing specific enantiomers of 4-amino-4,5-dihydro-2-furancarboxylic acid and $C_{1-6}$ lower alkyl esters thereof. These compounds are γ-aminobutyric acid transaminase inhibitors useful in the treatment of epilepsy.

5 Claims, No Drawings

INTERMEDIATES FOR THE SYNTHESIS OF 4-AMINO-4,5-DIHYDRO-2-FURANCARBOXYLIC ACID

CROSS-REFERENCE TO RELATED APPLICATION

This is a continuation, of application Ser. No. 540,745, filed Oct. 11, 1983, now abandoned.

This invention relates to the preparation of the individual enantiomers of 4-amino-4,5-dihydro-2-furancarboxylic acid, the lower alkyl esters thereof and to the intermediary compounds produced by the process.

4-Amino-4,5-dihydro-2-furancarboxylic acid, as well as its alkyl esters, are potent γ-aminobutyric acid transaminase inhibitors which are useful in the treatment of epilepsy. Thus, in view of its use as a chemotherapeutic agent it is of importance that the compounds be available in the individual enantiomeric forms. Of course, it is possible to subject a racemic mixture of these γ-aminobutyric acid inhibitors to resolution techniques utilizing available resolving acids according to generally known techniques but, in view of the expensive processes involved in the synthesis of 4-amino-4,5-dihydro-2-furancarboxylic acid it is preferred to obtain the desired enantiomer by the use of discriminating processes which maintain the stereo-specificity of the starting material.

In the process of this invention we have chosen to utilize either the D- or the L- forms of glutamic acid-γ-alkyl esters, preferably the methyl ester; the L-isomer producing the (S) form of 4-amino-4,5-dihydro-2-furancarboxylic acid while the D-form yields the (R) enantiomer. It should therefore be noted that in the description and illustrations of the process steps of this invention the enantiomeric form of the final product, as well as all of the intermediate compounds produced by the individual steps of this process, will be similar to that of the starting glutamic acid. In addition to its use in preparing either the R or the S enantiomers, the process may be adapted to the preparation of the racemic mixture by starting with the racemic mixture of the glutamic acid. Further, although the methyl ester of glutamic acid is utilized as the starting material, other lower alkyl esters may similarly be employed in the event such esters are desired as the final product.

Starting with the γ-methyl ester of the D-, L-, or the DL forms of glutamic acid, the amine moiety is protected by the formation of any of the known N-protecting groups by procedures well known in the art, although in practice it is preferred to utilize the t-butoxycarbonyl protective group which is prepared by reacting the ester with di-t-butyldicarbonate in the presence of a basic catalyst, preferably consisting of dioxane:water and triethylamine. The reaction is effected by contacting the reagents together under ice-bath conditions. The so-obtained N-protected compound is subjected to an anhydride formation and selective sodium borohydride reduction of the newly formed anhydride to its alcohol. The anhydride formation is performed with stoichiometric amounts of isobutylchloroformate, in the presence of triethylamine under vigorous stirring conditions whilst maintaining the temperature of the reaction mixture at cold temperatures and under an argon (or other inert gas) atmosphere. The sodium borohydride reduction is effected at temperatures less than 15° C.

The hydroxy moiety of the so-obtained methyl 4-[[(1,1-dimethylethoxy)carbonyl]amino]-5-hydroxypentanoate is silylated by reaction with t-butyldimethylsilyl chloride under strongly basic conditions (using 4-dimethylaminopyridine and triethylamine) at low temperatures, preferably at about 0° C. Utilizing freshly prepared lithium diisopropylamine under an inert atmosphere (argon) an enolate anion is formed (on the carbon atom adjacent the $CO_2CH_3$ ester group) and the so-formed enol is subjected to silylation with trimethylsilyl chloride to form a ketene acetal. (Concurrently therewith, the N-atom is also silylated). The silyl ketene acetal is then subjected to a strong oxidizing agent, (i.e., a mineral acid, preferably a per acid such as m-chloropexoxybenzoic acid) to epoxidize the olefin. Treatment of this product leads to methyl [[(1,1-dimethylethoxy)carbonyl]amino]-5-[[(1,1-dimethylethyl]-dimethylsilyl]oxy]-2-hydroxypentanoate which is oxidized with pyridinium dichromate to form an α-keto ester.

The α-keto ester is hydrolized with aqueous perchloric acid (or other equivalently functioning acid such as hydrochloric or sulfuric acids) to remove the silyl group and, in the process of its removal ring cyclization occurs to form a hemi-ketal, which ketal is dehydrated with thionyl chloride in the presence of pyridine to yield a methyl 4-[[(1,1-dimethylethoxy)carbonyl]amino]-4,5-dihydro-2-furancarboxylate. Although it is feasible to deprotect the amine function of the foregoing product(s) prior to hydrolysis of the ester group, it is preferred to convert the ester to its acid prior to deprotecting the amine and then, if desired, re-esterify the acid compound.

In effecting the hydrolysis it is preferred to utilize methanol in THF in the presence of aqueous lithium hydroxide, keeping the reaction mixture at ice-bath temperatures. The removal of the t-butoxycarbonyl protecting group is achieved by reacting the product of the previous step (preferably the acid form) with freshly prepared trifluoroacetic acid whilst under an inert atmosphere (e.g., argon) at ice-bath temperatures.

An alternate method for the preparation of the α-keto ester is to subject the silyl ketene acetal to oxygen (in its in situ-prepared singlet state) by bubbling oxygen through the reaction mixture and irradiating the mixture with a 450 watt Hanovia lamp (Ace Glass) filtered through pyrex. The oxygen is sensitized in situ using standard techniques such as by contacting the silyl ketene acetal with hematoporhyrin.

The foregoing process steps are specifically described by the following examples it being understood that obviously equivalent functioning steps are embraced herein.

EXAMPLE I (S)-4-Amino-4,5-dihydro-2-furancarboxylic Acid

Step A: N-[(1,1-dimethylethoxy)carbonyl]-L-glutamic acid-5-methyl ester

L-glutamic acid-γ-methyl ester (32.2 g, 0.2 moles) was suspended in 250 ml of dioxane-water (1:1 by volume) and triethylamine (42.0 ml, 0.3 moles) was added in one portion. The resultant solution was cooled in an ice bath and di-t-butyldicarbonate (50.6 ml, 0.22 moles) added in portions at a rate to control frothing. The cooling bath was removed after the addition was completed and the reaction mixture was stirred at room temperature overnight. The reaction mixture was concentrated to one-half its original volume on a rotovap and then diluted with 100 ml of water and 250 ml of ethyl acetate. This mixture was poured into a separatory funnel, the layers separated and the aqueous phase washed once more with 250 ml of ethyl acetate. 350 ml of ethyl acetate was then added to the separatory funnel and the aqueous phase acidified by the addition 150 ml of 1 M hydrochloric acid in 25 ml portions, shaking after each addition. The acidified aqueous layer was extracted with 2×100 ml of ethyl acetate. The combined organic extracts were washed once with 0.5 M hydrochloric acid and once with brine, dried over magnesium sulfate, filtered and concentrated to an oil on a rotovap. Further concentration on a vacuum pump gave the desired compound as an oil (45.1 g, 86%). Trituration with ether-hexane gave a white solid, m.p. 74°–77° C. (uncorrected). NMR (CDCl$_3$) δ 1.46 (s, 9H, —C(CH$_3$)$_3$), 1.84–2.60 (m, 4H, —CH$_2$—CH$_2$), 3.67 (s, 1H, —OCH$_3$), 4.08–4.50 (m, 1H, —CH—N), 5.10–5.47 (m, 1H, —NH), 11.00 (br s, 1H, —CO$_2$H). Anal. Calcd. for C$_{11}$H$_{19}$NO$_6$: C, 50.57; H, 7.33; N, 5.36. Found: C, 50.40; H, 7.69; N, 5.08.

Step B: Methyl 4-[[(1,1-dimethylethoxy)carbonyl]amino]-5-hydroxypentanoate

N-t-butoxycarbonyl-L-glutamic acid-γ-methyl ester (24.8 g, 94.9 mmoles) was dissolved in 400 ml of tetrahydrofuran under argon and cooled to −23° C. in a carbon tetrachloride-dry ice bath. Triethylamine (13.2 ml, 94.9 mmoles) was added to the stirred solution and, after five minutes, isobutylchloroformate (12.3 ml, 94.9 mmoles) was syringed in. Vigorous stirring was maintained during the isobutylchloroformate addition and a white precipitate began to form approximately one-half way into the addition. The resultant suspension was stirred at −23° C. for ten minutes and then stirring was ceased and the precipitate allowed to settle for five minutes. This suspension was then transferred, using a transfer needle and an argon stream, to a rapidly stirred solution of sodium borohydride (10.8 g, 0.28 moles) in 250 ml of water, precooled to 0°–5° C. in an ice bath. The sodium borohydride solution was contained in a three-neck, three liter flask equipped with an overhead stirrer and an internal thermometer. Addition to the sodium borohydride solution was at a rate such that the internal temperature was maintained at less than 15° C. at all times. Frothing occurred and ice was added to the sodium borohydride solution to aid cooling. Forty minutes after the addition was completed, the reaction mixture was poured into a separatory funnel containing 500 ml of methylene chloride and 300 ml of water. The layers were separated and the alkaline aqueous phase was extracted with 2×250 ml of methylene chloride. The combined organic extracts were washed with 400 ml of a mixture composed of (6:1:1) brine:1 M hydrochloric acid:water, dried over magnesium sulfate, filtered and concentrated on a rotovap to an oil. Flash chromatography on a 6×15 cm column using first 30% ethyl acetatehexane (1 liter) and then 70% ethyl acetate-hexane gave the desired compound as a water white oil (19.3 g, 82%). NMR (CDCl$_3$) δ 1.41 (s, 9H, —C(CH$_3$)$_3$), 1.55–2.08 (m, 2H, —CH$_2$—), 2.41 (t, 2H, J=7.5 Hz —CH$_2$CO$_2$) 3.48–3.79 (m, 3H, —CH—N and —CH$_2$—O), 3.63 (s, 3H, —OCH$_3$), 5.06–5.33 (m, 1H, —NH). Anal. Calcd. for C$_{11}$H$_{21}$NO$_5$: C, 53.43; H, 8.56; N, 5.66. Found: C, 53.51; H, 8.49; N, 5.49.

Step C: Methyl 4-[[(1,1-dimethylethoxy)carbonyl]amino]-5-[[(dimethylethyl)dimethylsilyl]oxy]pentanoate The alcohol (19.25 g, 77.8 mmoles) was dissolved in 200 ml of methylene chloride and cooled in an ice bath. t-Butyldimethylsilyl chloride (11.38 g, 75.5 mmoles), 4-dimethylaminopyridine (670 mg, 5.5 mmoles) and triethylamine (14.1 ml, 0.10 moles) were then added, in that order, with stirring. The cooling bath was removed and the reaction mixture stirred at room temperature overnight. The reaction mixture was poured into 200 ml of methylene chloride and 150 ml of water contained in a separatory funnel. The layers were separated and the organic phase washed with 2×150 ml of 0.5 M hydrochloric acid and once with brine. The organic layer was then dried over magnesium sulfate, filtered and concentrated on a rotovap to a brown oil. Flash chromatography on a 7×15 cm column using 12% ethyl acetate-hexane gave the desired compound as a water white oil (21.8 g, 80%). NMR (CDCl$_3$) δ 0.03 (s, 6H, —Si(CH$_3$)$_2$), 0.89 (s, 9H, —SiC(CH$_3$)$_3$), 1.42 (s, 9H, —OC(CH$_3$)$_3$), 1.67–2.00 (m, 2H, —CH$_2$—), 2.39 (t, 2H, J=7.5 Hz, —CH$_2$CO$_2$), 3.48–3.77 (m, 3H, —CH—N and —CH$_2$—O), 3.63 (s, 3H, —OCH$_3$), 4.42–4.78 (m, 1H, —NH). Anal. Calcd for C$_{17}$H$_{35}$NSiO$_5$: C, 56.47; H, 9.76; N, 3.87. Found: C, 56.52; H, 9.61; N, 4.14.

Step D: 1,1-Dimethyl-[1-[[(1,1-dimethylethyl)silyl]oxy]methyl]-4-methoxy-4-[(trimethylsilyl)oxy]-3butenyl]carbamate Diisopropylamine (19.44 ml, 0.14 moles) was dissolved in 150 ml of tetrahydrofuran and cooled to −78° C. under argon. n-Butyl lithium (74.5 ml of a 1.78 M solution in hexane, 0.13 moles) was syringed in and the solution stirred for fifteen minutes. The ester (21.8 g, 60.29 mmoles), dissolved in 30 ml of tetrahydrofuran and precooled to −78° C., was then added over an eight to ten minute time span using a transfer needle and an argon stream. The resultant solution was stirred for five minutes and then trimethylsilyl chloride (23.0 ml, 0.18 moles) was added by syringe over three to five minutes. The reaction mixture was allowed to warm slowly to room temperature over a one and one-half hour period. The white suspension was concentrated at ambient temperature on a rotovap, diluted with 200 ml of hexane and suction filtered. The filtered material was washed with a further 15 ml of hexane and the combined filtrate concentrated at ambient temperature on a rotovap, followed by a vacuum pump, to give the desired compound as a pale yellow, oily liquid (30.5 g, 100%).

Step E: Methyl 4-[[(1,1-dimethylethoxy)carbonyl]amino]-5-[[(1,1-dimethylethyl)dimethylsilyl]oxo]-2-hydroxypentanoate The silyl ketene acetal (33.4 g, 66.4 mmoles) was dissolved in 400 ml of hexane, under argon, and cooled in an ice bath. The reaction flask was also fitted with an overhead stirrer to ensure vigorous agitation. 100% m-chloroperoxybenzoic acid was added in one portion to the vigorously stirred solution and the reaction mixture stirred at 0°–5° C. for one hour. The reaction mixture was then suction filtered to remove a white solid, the solid washed with an additional 500 ml of cold hexane and the combined filtrate poured into a separatory funnel containing 500 ml of ether and 300 ml of saturated sodium bicarbonate. The layers were separated and the organic phase washed with 3×300 ml of a mixture composed of (1:1) saturated sodium carbonate: water followed by 300 ml of brine. The organic layer was dried over magnesium sulfate, filtered and concentrated on a rotovap. The residue was dissolved in 200 ml of methanol and 35 ml of water and stirred at room temperature for seven hours. The reaction mixture was then concentrated to one-half its original volume on a rotovap and poured into a separatory funnel containing 300 ml of methylene chloride and 100 ml of a mixture composed of (2:1) brine:water. The layers were separated and the organic phase extracted with an additional 50 ml of methylene chloride. the combined organic extracts were dried over magnesium sulfate, filtered and concentrated on a rotovap. Flash chromatography on a 7×15 cm column using hexane (1.5 l) followed by 5% ethyl acetate-hexane (1.5 l) and finally 25% ethyl acetate-hexane (2.5 l) afforded the desired compound as an oil (6.0 g, 24%) and allowed for the recovery of 5 grams (21%) of methyl 4-[[(1,1-dimethylethoxy)carbonyl]amino]-5-[[(1,1-dimethylethyl)dimethylsilyl]oxy]pentanoate which could be recycled. NMR (CDCl$_3$) δ 0.09 (s, 5H, —Si(CH$_3$)$_2$), 0.91 (s, 9H, —Si—C(CH$_3$)$_3$), 1.48 (s, 9H, —OC(CH$_3$)$_3$), 1.68-2.21 (m, 2H, —CH$_2$—), 3.43-4.10 (m, 4H, —CH$_2$—O and —CH—N and —OH), 3.75 (s, 3H, —OCH$_3$), 4.10-4.42 (m, 1H, —CH—O), 4.58-5.16 (m, 1H, —NH). Anal. Calcd for C$_{17}$H$_{35}$NSiO$_6$: C, 54.08; H, 9.34; N, 3.71. Found: C, 54.19; H, 9.53; N, 3.41.

Step F: Methyl 4-[[(1,1-dimethylethoxy)carbonyl]amino]-5-[[(1,1-dimethylethyl)dimethylsilyl]oxy]-2-oxopentanoate To a solution of the alcohol (5.8 g, 15.4 mmoles) in 150 ml of methylene chloride was added pyridinium dichromate (28.9 g, 76.8 mmoles) in portions. After the addition was completed, the suspension was stirred at room temperature for three days. An additional 2.9 g (7.7 mmoles) of pyridinium dichromate was added on the fourth and again on the fifth days. A final 2.9 g of pyridinium dichromate was added on the eight day of stirring. After eleven days, the reaction mixture was diluted with 750 ml of ether while stirring vigorously. The reaction mixture was then suction filtered through celite/magnesium sulfate. The filter pad was washed with an additional 350 ml of ether and the combined filtrate concentrated on a rotovap to approximately 200 ml. This residue was washed with 2×50 ml of 0.5 M hydrochloric acid and once with 50 ml of brine. The organic phase was then dried over magnesium sulfate, filtered and concentrated to a brown oil. Flash chromatography on a 5×15 cm column using 15% ethyl acetatehexane as the eluant gave the desired compound as a water white oil (4.44 g, 77%). NMR (CDCl$_3$) δ 0.06 (s, 6H, —Si(CH$_3$)$_2$), 0.89 (s, 9H, —SiC(CH$_3$)$_3$), 1.44 (s, 9H, —OC(CH$_3$)$_3$), 3.03 (d, 2H, J=6 Hz, —CH$_2$CO—), 3.68 (d, 2H, J=4 Hz, —CH$_2$—O), 3.85 (s, 3H, —OCH$_3$), 3.96-4.30 (m, 1H, —CH—N), 4.79-5.12 (m, 1H, —NH). Anal. Calcd for C$_{17}$H$_{33}$NSiO$_6$: C, 54.37; H, 8.86; N, 3.73. Found: C, 54.26; H, 9.13; N, 3.48.

Alternate synthesis for preparation of product of Step F:

A solution of the silyl ketene acetal (489 mg, 0.97 mmoles) of Step D and hematoporphyrin (2.5 mg) in 4:1 CH$_3$CN:CHCl$_3$ (5 ml) was chilled in an ice bath. Oxygen gas was bubbled through the solution at about 250 ml/min while irradiating with a 450 watt Hanovia lamp (Ace Glass) filtered through pyrex.

After 30 min, an aliquot was removed and quenched in saturated NaHCO$_3$ solution. TLC analysis showed only a trace of the starting ester.

The solution was purged with argon and treated with 0.75 ml Et$_3$N (5.5 eq.) for 90 min at 0° C. The solution was diluted with ether, washed with 0.5 N HCl, saturated NaHCO$_3$ solution and brine, and dried over MgSO$_4$. Filtration and concentration of the filtrate produced an oil (305 mg) from which 195 mg (54%) of the α-ketoester was isolated by flash chromatography. This sample displayed the same spectral characteristics and TLC behavior as a sample of α-ketoester prepared by alternate methods.

Step G: Methyl 4-[[(1,1-dimethylethoxy)carbonyl]amino]tetrahydro-2-hydroxy-2-furancarboxylate To a solution of the α-ketoester (3.76 g, 10.0 mmoles) in 35 ml of tetrahydrofuran was added 6.5 ml of 2% aqueous perchloric acid. The resultant solution was stirred at room temperature for five hours (TLC shows reaction to be complete) and then poured into a separatory funnel containing 200 ml of ethyl acetate and 50 ml of a mixture composed of (3:1:1) brine: water:saturated aqeuous sodium bicarbonate. The layers were separated and the aqueous phase extracted 2×20 ml with methylene chloride. The combined organic extracts were dried over magnesium sulfate, filtered and concentrated on a rotovap. Flash chromatography on a 5×12 cm column using 45% ethyl-hexane as the eluant gave the desired compound, a water white oil (2.18 g, 84%), as a mixture of epimers. NMR (CDCl$_3$) δ 1.42 (s, 9H, —OC(CH$_3$)$_3$), 1.88-2.78 (m, 2H, —CH$_2$—C—CO$_2$), 3.76 and 3.78 (s, 3H, —OCH$_3$), 3.82-4.51 (m, 3H, —CH—N and —CH$_2$—O), 4.40 and 4.68 (br s, 1H, —OH), 5.18-5.63 (m, 1H, —NH). Anal. Calcd for C$_{11}$H$_{19}$NO$_6$: C, 50.57; H, 7.33; N, 5.36. Found: C, 50.82; H, 7.47; N, 5.37.

Step H: Methyl 4-[[(1,1-dimethylethoxy)carbonyl]amino]-4,5-dihydro-2-furancarboxylate To a solution of the alcohol (2.48 g, 9.45 mmoles) in 40 ml of methylene chloride, cooled in an ice bath under argon, was added pyridine (1.54 ml, 18.98 mmoles) and then thionyl chloride (0.69 ml, 9.49 mmoles). After fifteen minutes, the cooling bath was removed and the reaction mixture was stirred at room temperature for an additional five hours. The reaction mixture was then added to a separatory funnel containing 60 ml of methylene chloride and 35 ml of 0.5 M hydrochloric acid. The layers were separated and the organic phase washed with 25 ml of brine, dried over magnesium sulfate, filtered and concentrated on a rotovap to a white solid. Flash chromatography on a 5×15 cm column using 35% ethyl acetate-hexane as the eluant gave the desired compound as a white solid (1.80 g, 78%), m.p. 94°-96° C. (uncorrected). NMR (CDCl$_3$) δ 1.40 (s, 9H, —OC(CH$_3$)$_3$), 3.76 (s, 3,—OCH$_3$), 4.23 (dd, 1H, J=4.5 and 10.5 Hz, —CH—O), 4.50 (dd, 1H, J=9.0 and 10.5 Hz, —CH—O) 4.80-5.27 (m, 2H, —NH and —CH—N), 5.90 (d, 1H, J=3 Hz, —C=CH). Anal. Calcd for C$_{11}$H$_{17}$NO$_5$: C, 54.31; H, 7.04; N, 5.76. Found: C, 54.07; H, 7.24; N, 5.47.

Step I:
4-[[(1,1-dimethylethoxy)carbonyl]amino]-4,5-dihydro-2-furancarboxylic acid To a solution of the ester (1.80 g, 7.40 mmoles) in 25 ml of tetrahydrofuran and 35 ml of methanol, cooled in an ice bath, was added 16.28 ml of 1 M aqueous lithium hydroxide with stirring. The reaction mixture was stirred at ice bath temperature for ninety minutes and then poured into a separatory funnel containing 400 ml of ethyl acetate and 150 ml of a mixture composed of (8:1:1) brine:2 M hydrochloric acid:water. The layers were separated and the organic phase dried over magnesium sulfate, filtered and concentrated on a rotovap to a white solid. The solid was redissolved in 125 ml of ethyl acetate and washed with 2×20 ml of 0.1 M hydrochloric acid followed by 25 ml of brine. The organic phase was dried over magnesium sulfate, filtered and concentrated on a rotovap to give the desired compound as a white solid (1.55 g, 91%), m.p. 117°–120° C. (decomposes; uncorrected). NMR (CDCl$_3$) δ 1.43 (s, 9H, —OC(CH$_3$)$_3$), 4.25 (dd, 1H, J=4.5 and 10.5 Hz, —CH—O), 4.52 (t, 1H, J=10.5 Hz, —CH—O), 4.70–5.28 (m, 2H, —NH and —CH—N), 5.98 (d, 1H, J=3 Hz, —C=CH), 8.86 (br s, 1H, —CO$_2$H). Anal. Calcd for C$_{10}$H$_{15}$NO$_5$: C, 52.40; H, 6.60; N, 6.11. Found: C, 52.24; H, 6.66; N, 5.92.

Step J: (S)-4-Amino-4,5-dihydro-2-furancarboxylic acid

To 4.5 ml of freshly distilled trifluoroacetic acid, under argon and cooled in an ice bath, was added the acid (774 mg, 3.38 mmoles) in one portion with stirring. Immediate gas evolution was noted and, after fifteen minutes, the solution was added dropwise to 125 ml of cold, anhydrous ether with rapid stirring. The resultant white precipitate was stirred for fifteen minutes at ice bath temperature and then filtered under argon. The collected white solid was washed three times with 10 ml of cold anhydrous ether and then dried under vacuum. Chromatography on a 2×10 cm bed of ion exchange resin (Biorad AG50W-X8; H+ from 50–100 mesh) using 2 M ammonium hydroxide as the eluant gave the desired compound as a white solid (305 mg, 70%), m.p. 193°–195° C. (decomposes; uncorrected). NMR (CF$_3$CO$_2$D) δ 4.73–5.17 (m, 3H, —CH$_2$O and —CH—N), 6.34 (d, 1H, —CH=C, J=3 Hz). Anal. Calcd for C$_5$H$_7$NO$_3$: C, 46.51; H, 5.46; N, 10.85. Found: C, 46.30; H, 5.48; N, 10.55.

We claim:

1. Compounds of the group consisting of;
1,1-Dimethyl-[1-[[(1,1-dimethylethyl)silyl]oxy]methyl]-4-methoxy-4-[(trimethylsilyl)oxy]-3-butenyl[carbamate;

Methyl 4-[[(1,1-dimethylethoxy)carbonyl]amino]-5-[[(1,1dimethylethyl dimethylsily]oxy]-2-hydroxypentanoate;

Methyl 4-[[(1,1-dimethylethoxy carbonyl]amino-5-[[(1,1-dimethylethyldimethylsilyl]oxy]2-oxopentanoate;

Methyl 4-[[(1,1-dimethylethoxy carbonyl]amino]tetrahydro-2-hydroxy-2-furancarboxylate;

Methyl 4-[[(1,1-dimethylethoxy)carbonyl]amino]-4,5-dihydro-2-furancarboxylate; and 4-[[(1,1-dimethylethoxy)carbonyl]amino]-4,5-dihydro-2-furancarboxylic acid.

2. A compound of claim 1, said compound being 4-[[(1,1-dimethylethoxy) carbonyl]amino]-4,5-dihydro-2-furancarboxylic acid.

3. A compound of claim 1, said compound being Methyl 4-[[(1,1-dimethylethoxy)carbonyl]amino]-5-[[(1,1-dimethylethyl)dimethylsilyl]oxy]-2-oxopentanoate.

4. A compound of claim 1, said compound being Methyl 4-[[(1,1-dimethylethoxy)carbonyl]amino]tetrahydro2-hydroxy-2-furancarboxylate.

5. A compound of claim 1, said compound being Methyl 4-[[(1,1-dimethylethoxy)carbonyl]amino]-4,5-dihydro-2-furancarboxylate.

* * * * *